United States Patent
Wiklund

Patent Number: 6,017,327
Date of Patent: *Jan. 25, 2000

[54] ACCESSORY TO SYRINGES

[76] Inventor: Ernst Sigurd Gustaf Folke Wiklund, Lindevägen 40, Stockholm, Sweden, S-120 48

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,348

[22] PCT Filed: Mar. 6, 1996

[86] PCT No.: PCT/SE96/00295

§ 371 Date: Aug. 27, 1997

§ 102(e) Date: Aug. 27, 1997

[87] PCT Pub. No.: WO96/27401

PCT Pub. Date: Sep. 12, 1996

[51] Int. Cl.[7] .................................................. A61M 5/178
[52] U.S. Cl. .................................. 604/169; 128/DIG. 26
[58] Field of Search .................................... 604/159, 256, 604/257, 258, 261, 280, 283, 177, 170, 179, 169, 174, 178; 128/DIG. 26

[56] References Cited

U.S. PATENT DOCUMENTS

| | | | |
|---|---|---|---|
| 3,802,433 | 4/1974 | Raven | 604/283 |
| 5,057,093 | 10/1991 | Clegg et al. | 604/256 X |
| 5,098,405 | 3/1992 | Peterson et al. | 604/256 X |
| 5,098,410 | 3/1992 | Kerby et al. | 604/256 |
| 5,203,771 | 4/1993 | Melker et al. | 604/283 X |
| 5,250,038 | 10/1993 | Melker et al. | 604/283 X |
| 5,263,944 | 11/1993 | Vidal et al. | 604/256 |
| 5,389,100 | 2/1995 | Bacich et al. | 604/283 X |

FOREIGN PATENT DOCUMENTS 355946  9/1971  Sweden.

*Primary Examiner*—Wynn Wood Coggins
*Assistant Examiner*—A. T. Nguyen
*Attorney, Agent, or Firm*—Pennie & Edmonds LLP

[57] ABSTRACT

An accessory for temporary, contamination-free holding of closing stoppers used for syringes and other medical care devices, where the accessory comprises a stopper designed for coupling to a recess in another existing stopper or a carrier that can be combined with a stopper. The carrier has a lower part, which may be designed as a substitute for an existing stopper; a mid-piece, which is inserted in or over an existing stopper; a rider for placing over a curved surface such as a syringe body; or a carrier-foot for fastening onto suitable surfaces.

19 Claims, 4 Drawing Sheets

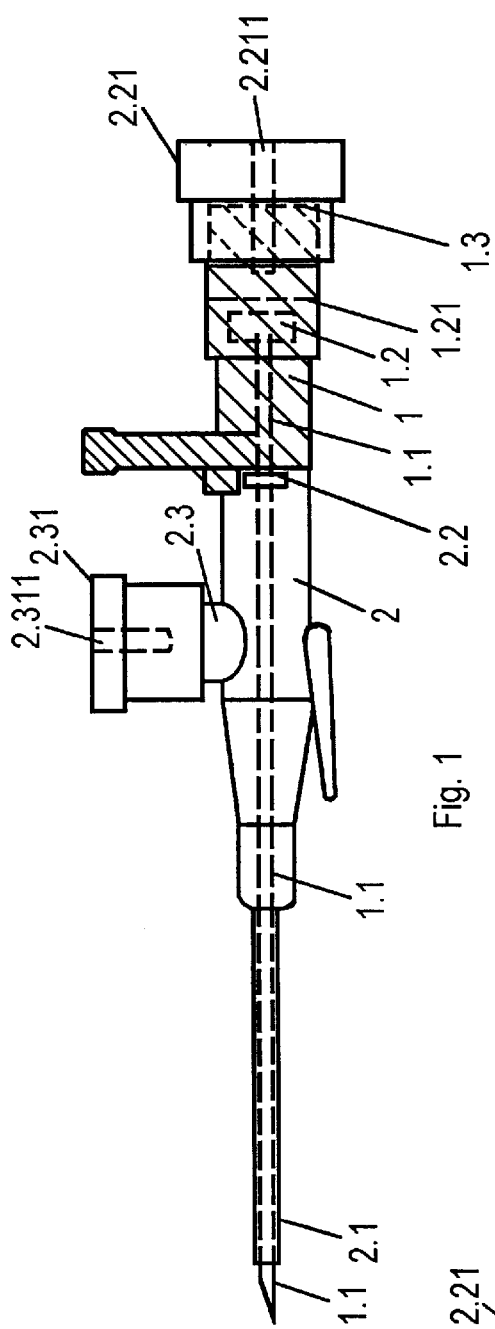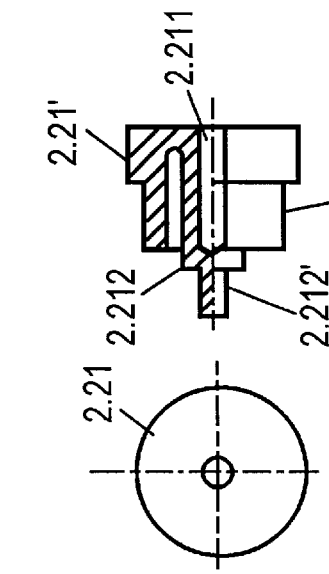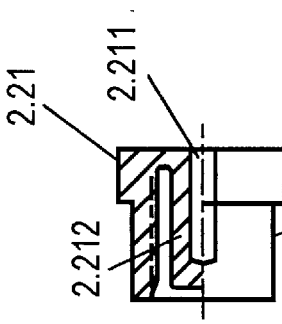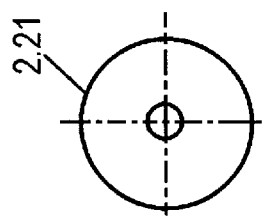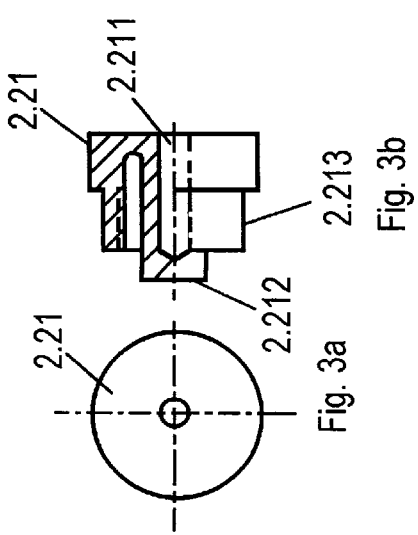

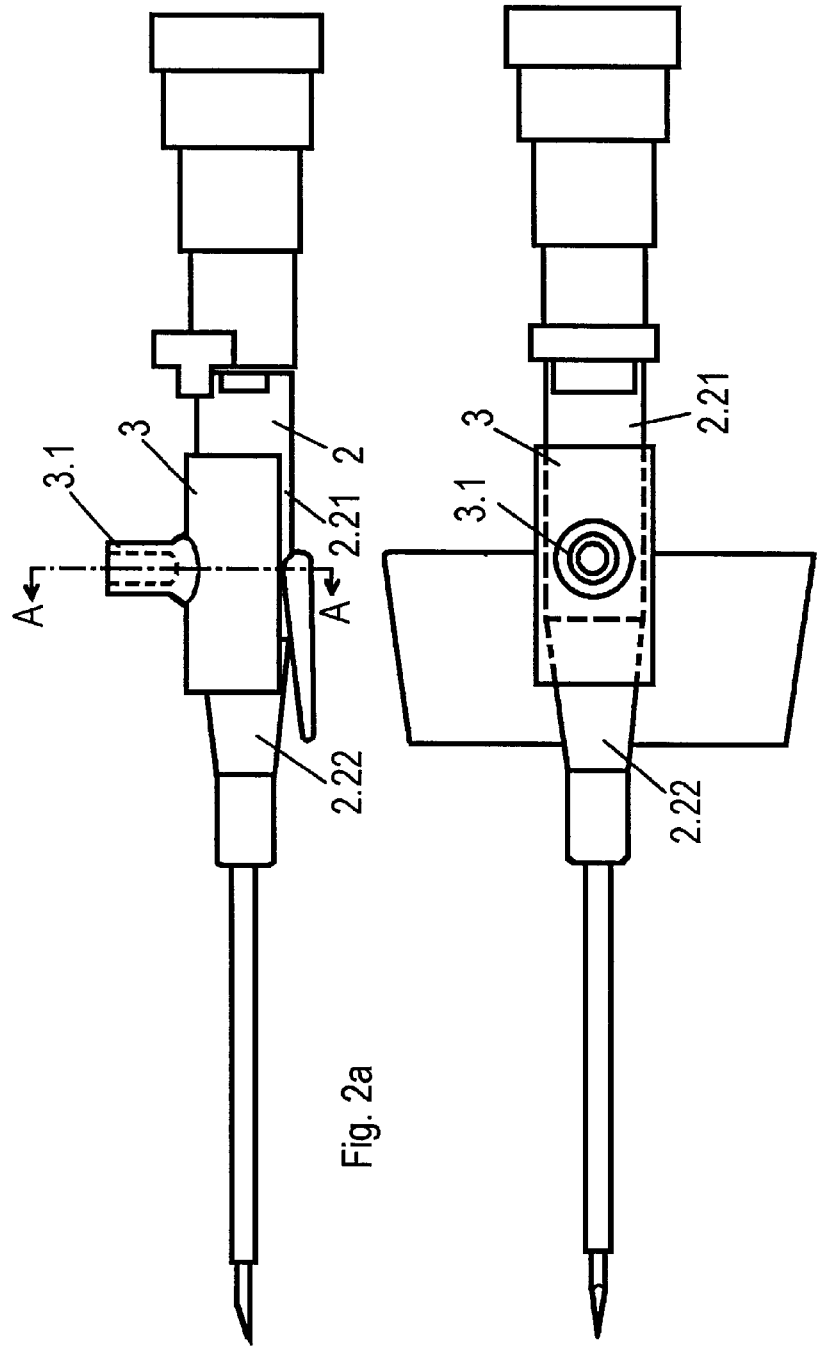
Fig. 2a
Fig. 2b
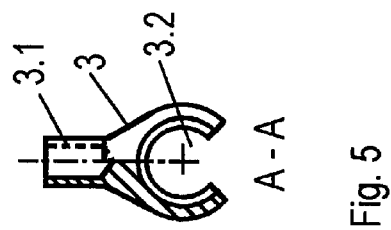
Fig. 5

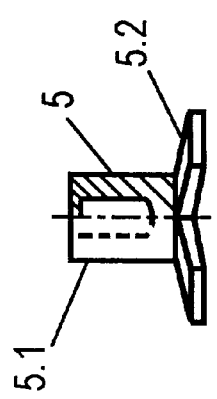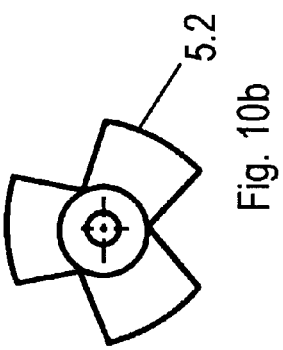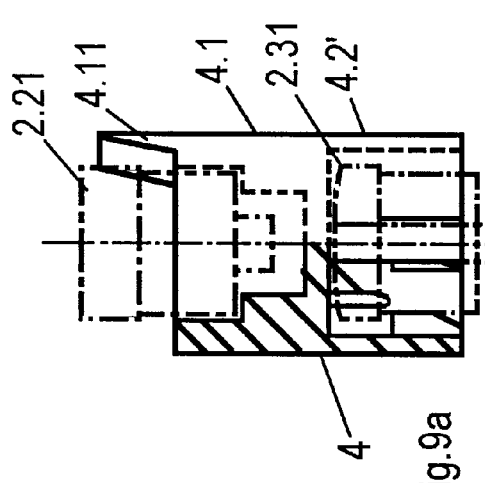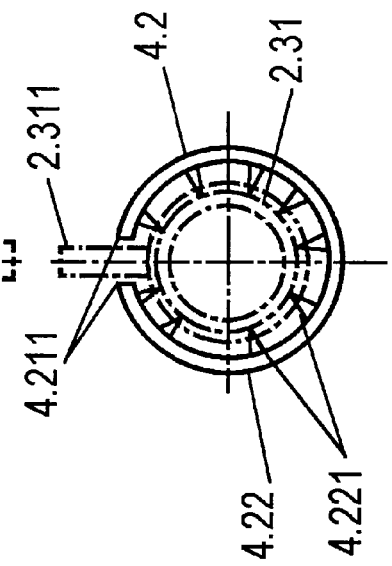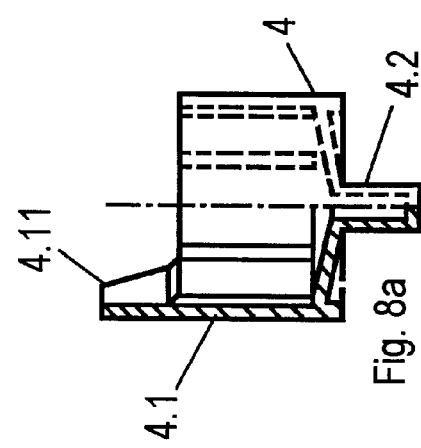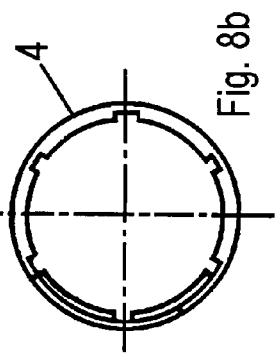

ACCESSORY TO SYRINGES

TECHNICAL FIELD

The invention relates to a method and accessory for the contamination-free keeping of stoppers used in medical care. The fitting comprises a stopper or carrier which is temporarily placed upon syringes or other equipment to prevent entry of contamination while awaiting use of the syringe.

BACK GROUND ART

The medical care needs often to establish connection to the patient's hypodermic tissues via syringes, tubes or containers of different kinds. The connection must be established with total sterility. Leakage and unwanted contact must be avoided as far as possible. Such unintended contact, especially with blood and blood vessels, may involve a very serious risk of infection.

Examples of treatments requiring blood vessel connection are blood transfusion inclusive blood giving, blood sampling assisted by test containers under negative pressure, and intravenous supply of medicine, nourishment or just liquid for blood volume expansion, commonly called a drip.

A frequently used syringe for insertion in blood vessels of different kinds has a tube body with a channel that continues in a thin and soft plastic tube. The rear port of the tube body is shaped as a conical cavity and, at the beginning, closed by a hollow needle and a needle body, the rear part of which has a transparent signal chamber, which gets filled with blood, when satisfactory blood vessel contact has been established. The rear wall of the signal chamber is liquid-tight and prevents blood shedding through the rear opening of the needle body. This opening is used for temporary placement of a stopper intended for tightening the rear port of the tube body, when the needle has been withdrawn.

To establish a blood vessel connection one choses a suitable, superficial blood vessel (vein or artery depending upon type of treatment) and tries to direct the tip of the puncture needle to penetrate the skin just over the chosen blood vessel, so that the tip hits the vessel centrally and, after penetration of the vessel wall, with the plastic tube can be directed into the blood path. When the above mentioned transparent room behind the needle starts filling with blood, the syringe is advanced a little (about 2 mm) to ensure complete penetration of the vessel wall. Then the needle body with the belonging puncture needle is kept still, while the tube is advanced so that the needle tip no longer is in front of the end of the plastic tube. This is done to prevent the needle tip from hurting the vessel wall. Finally the syringe is advanced to its desired position and kept there.

After that the puncture-needle is withdrawn. To prevent blood shedding through the rear opening of the tube body, which has been tightened by the needle body, the withdrawal is begun by the operator by compressing, with one of his or her hands, the skin area over the tip of the plastic tube, until he or she has withdrawn the puncture needle and applied the intended stopper in the rear end of the tube body.

This is a critical moment concerning leakage. As seen above the operator has just one hand free (usually the right hand). The other hand is used for tissue compressing. With the free hand the operator has to loosen the stopper from the needle body and, without contaminating the stopper, move it to the rear end of the tube body. The needle body may have to be let free for grip changing before the stopper can be removed. The operation is not simple even under good circumstances in a ward unit. If it instead has to be done in a forth-rushing ambulance by personnel with little syringe handling education, the difficulties become even worse.

The risk is large that the needle body rolls away. The risk is also large that the stopper is dropped and lost and/or becomes contaminated before getting placed in the rear port of the tube body. In both cases the operator needs help, if not the whole operation should have to be repeated with a new sterile syringe.

Trials have been made earlier (The Swedish laid open publication no 355 946) to place the tube body stopper at one of the tube body's wings. This placing has shown to be less convenient, as the stopper gets in the way and hampers the vessel puncture.

The problem of sterile between-handling is not limited to blood vessel entries. It appears in a row of clinical situations for example irrigation (rinsing) at surgical operations and respirator treatments to mention a few examples. The circumstances at these situations are in high degree analogous with those at intravenous entry and the more detailed description is therefore limited to the circumstances at venous punctures.

SUMMARY OF THE INVENTION

The purpose of this invention is to solve the problem of between keeping and availability of stoppers under circumstances preventing contamination. According to this new method the stopper is coupled to the device so it does not hamper actual operation, is nearby and can be easily loosened and placed in the intended opening, without the risks mentioned above of getting lost or contaminated.

Further the invention concerns fittings to syringes of the type described above, i.e. consisting of a tube body and a needle body and other medical care devices with similar stoppers. The fitting may consist of a stopper designed for coupling to a recess in another existing stopper or a carrier, which may be combined with a stopper. The carrier has a lower part, which may be designed as a substitute for an existing stopper, a mid-piece, which is inserted in or over an existing stopper, a rider for placing over curved surfaces or a plane foot for fastening at suitable surfaces.

The requirement, that the coupling must be done without letting the stopper hamper the handling of the syringe, rules out earlier mentioned placing at one wing of the tube body. If the syringe is provided with an upper port and a stopper belonging to this port placing at its upper surface is preferred. Concerning syringes that do not have suitable surfaces for the temporary placing of the end stopper the stopper of the invention is combined with a carrier for instance in the shape of a rider, which can be placed at a suitable location at the tube body. Altered design of the tube body may also provide new surfaces suitable for temporary placing of the end stopper. The same is valid for other equipment, too.

For devices with a design that makes riders not suitable, the rider can be substituted with a carrier-foot according to the Swedish patent application no 9500800-9.

The coupling between the tube body and the stopper must be done so that no increased risks of contaminating surfaces with potential blood contact are produced. One possibility is that the coupling is done when the sterile packed syringe is taken from the package and before the surface, where the coupling takes place, has been touched. Another possibility is to protect the surface with a protecting tape until the coupling moment. The first possibility is preferred if stopper and syringe is in separate packages. The second may be of interest if the fitting is by-packed the syringe.

Coupling to an existing upper stopper can be done via a slender outgrowth 2.212' at the cone-formed closing part of the end stopper 2.212 designed to fit the recess in the upper tube body stopper 2.31 or another suitably seized recess at the tube body. The outgrowth may with advantage be designed as a rod passing through a bore in the stopper and being pressed in when the coupling is done.

Conical stoppers of this kind are often used in the medical care and are the subject of a standard that is usually called Luer-cone (ISO-standard 594/1-2).

An alternative to using a stopper as above is that the fitting consists of stopper 2.31' that substitutes the upper tube body stopper 2.31. The upper part of the substitute stopper is designed so that its form functionally matches the rear opening of the needle body and thus is suitable to serve as "parking place" for the existing end stopper. To prevent misunderstanding it should be remarked that the rear opening of the needle body is a blind port, the sole function of which is to keep and protect the end stopper from contamination, until it is used for closing the rear port of the tube body. All designs that fulfill this purpose thus match the rear opening of the needle body from the functional point of view.

It may for instances be an edge that surrounds a recess fitting the protruding conical closing part 2.212 of the end stopper 2.21 or a cone-formed, inner recess and an outer tube-formed part that together match the rear opening of the needle body, or an essentially conical tube-piece that by spring force engages the inner wall of the end stopper's mantle. Different variants and combinations of these designs may be used for different syringe types. Besides these already mentioned arrangements one may also use a design with a slitted or bead provided tube-piece, which by spring-force grasps around the outer mantle of the end-stopper.

As an alternative to modification of the upper tube body stopper a mid-piece may be used, which has a lover part with an outgrowth of the type mentioned for the end-stopper or a lover tube-formed part adapted for a suitable firm and flexible fit around the upper tube body stopper's upper part and an upper part that functionally matches the rear opening of the needle body, i.e. is designed analogously with the upper part of the alternative upper stopper described.

If the fitting is sold separately, the design with a tube-part grasping around the outer mantle of the end-stopper may be of special interest, as it, with relative ease, can be made to fit most of the syringe types that are present on the market. Besides this design is less demanding of complete sterility at the handling, as no surfaces that may meet blood have to be touched.

BRIEF DESCRIPTION OF THE DRAWINGS

FIG. 1 shows a syringe with an upper port.

FIG. 2*a* is side view of a syringe without upper port and provided with a rider for temporary placing of a tube body stopper of the invention.

FIG. 2*b* is a plan view of a syringe without an upper port and provided with a rider for temporary placing of a tube body stopper of the invention.

FIG. 3*a* depicts a cross-sectional view of the upper part of a typical prior art stopper.

FIG. 3*b* depicts a partially-sectioned side view of the stopper of FIG. 3*a*.

FIG. 4 shows a design of to FIG. 4*a* depicts a cross-sectional view of the upper part of a stopper according to the invention.

FIG. 4*b* depicts a partially-sectioned side view of the stopper of FIG. 4*a*.

FIG. 5 shows a section of a rider intended for use on syringes according to FIG. 2*a* along the line 5—5.

FIG. 8*a* depicts a partially sectioned side view of a mid-piece intended for use on syringes with an upper stopper and an upwards open recess in this stopper.

FIG. 8*b* depicts a cross-sectional view of the mid-piece of FIG. 8*a*.

FIG. 9*a* depicts a partially sectioned side view of a mid-piece intended for use at syringes with an upper stopper without upwards open recess.

FIG. 9*b* depicts a cross-sectional view of the mid-piece of FIG. 9*a*.

FIG. 10*a* depicts a partially sectioned side view of a carrier-foot, which can be used for application at equipment with plane surfaces.

FIG. 10*b* depicts a plan view of the carrier foot of FIG. 10*a*.

FIG. 11*a* depicts a cross-sectional view of the upper part of a typical prior art stopper.

FIG. 11*b* depicts a partially sectioned side view of the prior art stopper of FIG. 11*a*.

DETAILED DESCRIPTION OF THE PREFERRED EMBODIMENTS

Figure 6:
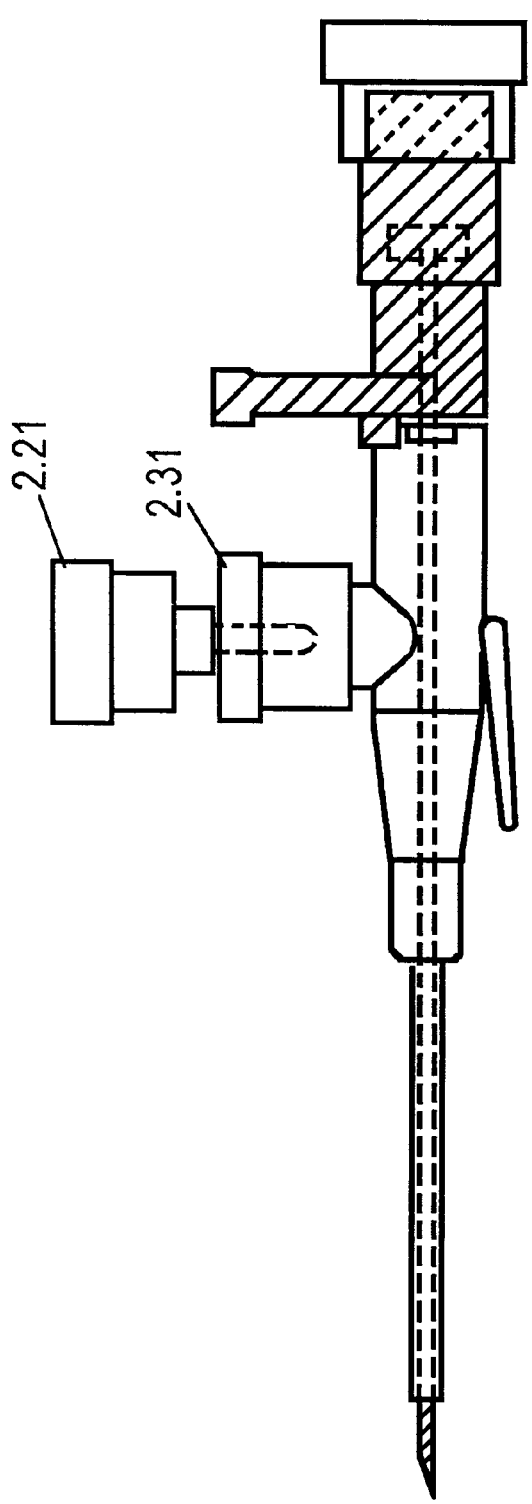
FIG. 6 shows a syringe like FIG. 1 provided with a stopper according to the invention placed upon the upper tube body stopper.
Figure 7:
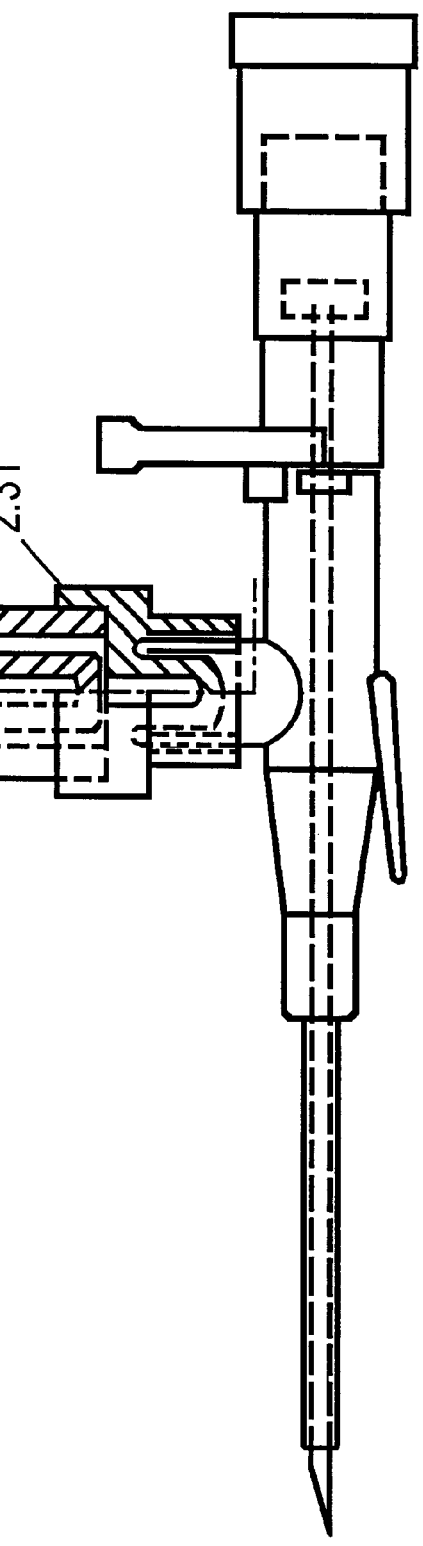
FIG. 7 shows a syringe like FIG. 1 provided with a variant of an upper tube body stopper according to the invention.

FIG. 1 shows one of the often used syringes for entry in blood vessels of different kinds. The syringe consists of a tube body 2 with a channel that continues in a thin and soft plastic tube 2.1. The rear opening of the tube body 2.2 is shaped as a conical cavity and, from the beginning, closed by the tube-formed needle 1.1 and the needle body 1, which has been marked by slanting lines. The rear part of the needle body has a transparent signal chamber 1.2, which gets filled with blood, when satisfactory blood path contact has been established. The rear wall 1.21 of the signal chamber 1.2 is liquid-tight and prevents blood shedding out of the rear opening 1.3 of the needle body. This opening is used for temporary placing of the stopper 2.31 intended for closing the rear opening 2.2 of the tube body, when the needle has been withdrawn. Beside the opening 2.2 the tube body 2 has another opening 2.3 used for connection to injectors etc. This opening in closed by the stopper 2.31, which centrally has an upwards open axial recess 2.311. Such recesses are, as a rule, present at stoppers of similar kinds and serve to prevent dimension changes at manufacturing by pressure moulding.

FIGS. 2*a* and 2*b* shows another often used syringe without upper port. Apart from that and the fact that it has been provided with a rider 3, placed over the tube body abreast with its wings and designed with a recess 3.1 for the stopper 2.2, the design of this syringe corresponds with the one according to FIG. 1.

FIGS. 3*a*, 3*b*, 11*a* and 11*b* show the stoppers, usually belonging to the syringes of FIG. 1 and 2, in larger scale. FIGS. 4*a* and 4*b* shows one design of a stopper according to the invention. In both cases the stopper has a protruding, central, slightly cone-formed part 2.212, the purpose of which is closing of the slightly conical opening 2.2 of the tube body 2 and a protecting, cylinder-formed mantle 2.213, which depending upon the supplier of the syringe may have different length and sometimes covers the closing part entirely. According to the design of FIGS. 4a and 4b the stopper is provided with a tapering outgrowth (length about twice the diameter) 2.212' of the conical part 2.212. The diamete r of the outgrowth is chosen so it with moderately firm coupling can be inserted into the recess 2.311 of the stopper 2.31. As mentioned above the outgrowth may with advantage be designed as a rod passing trough a bore in the stopper 2.31 and being pressed in, when the coupling is done.

FIG. 5 shows a rider, which can be used to get a suitable place for temporary keeping of the end-stopper of syringes lacking upper port. The lower part has a recess 3.2 in the shape of a cut cylinder with part of the mantle removed. The recess is made so the rider can be placed upon a syringe like FIG. 2 abreast with the wings. The upper part of the rider can have a recess 3.1 adapted for receiving a modified stopper or a mid-piece as above, which here accompanies the rider. Another better alternative is, of course, an upper part with principally the same design as the upper part of the mid-piece.

FIGS. 8a and 8b, 9a and 9b show two different designs of mid-pieces that have been found especially suitable. In the FIGS. 4.1 stands for the upper part and 4.2 respectively. 4.2' for the lower part. In FIGS. 8a and 8b the lower part 4.2 consists solely of an outgrowth adapted to fit into the recess of the upper stopper. In FIGS. 9a and 9b the lower part has been designed to fit over the upper stopper 2.31 even if it is lacking upwards open recess. Upper stoppers have as a rule a "strap" 2.311 that anchors it to the tube body. The mantle of the lower part of the mid-piece is therefore provided with a longitudinal recess 4.211.

FIGS. 10a and 10b shows a carrier-foot 5 that with advantage may be used at equipment with plane surfaces near the place, where the stopper is used. The footplate 5.2 should be prepared so it, after removing a protecting film, sticks to the surface permanently or temporary depending on the need. The upper part 5.1 may with advantage be designed analogously with the mid-pieces of the FIGS. 8 and 9.

Riders according to FIG. 5, carrier-feet as in FIGS. 10a and 10b and mid-pieces of the types shown in FIGS. 8a, 8b, 9a and 9b can be designed s o they can be used without sterilizing. A condition for this is that they in a reliable way can be handled without making contact between surfaces that may meet blood and tissues and not sterilised surfaces. To facilitate insertion of the stopper 2.21 in the upper part, without making unintended contacts, the upper part is provided with a guide rail 4.11 that makes the insertion of the stopper easier.

To amend the fit between the mid-piece and the upper stopper of the tube body the lower part of the mantle 4.22 may be provided with yielding edgings 4.221. Similar edgings may be used for the upper part too. Another alternative to effect required, firm keeping, without causing problems at loosening, is longitudinal notches or beads at the inner side of the tubes. The same is true, if applicable, for carrier-stoppers, riders and carrier-feet.

The new accessory may be marketed as a separate unit or by-packed the syringe or device. As already mentioned the rear opening of the needle body is a blind port, the sole purpose of which is keeping and protecting the end-stopper. A modified stopper or a mid-piece with an inserted stopper may be placed there, if the rear end of the needle body is modified. Another possibility is that a mid-piece is placed in the end-stopper's recess and moved to the upper stopper at the start of the operation. The proposed possibilities are examples and should not be considered as limiting the invention.

It is claimed:

1. A combination comprising a separate closing stopper and a blood vessel access device which includes a tubular body having a distal port that receives the closing stopper therein and a proximal portion that includes a needle, the improvement which comprises a fitting for temporary coupling with and support of the closing stopper when the closing stopper is removed from the distal port of the tubular body, which fitting comprises a separate carrier foot (5) having a base portion and a body portion extending from the base portion, wherein the body portion includes support means for temporary association of the stopper therewith when the stopper is removed from the distal port of the blood vessel access device.

2. The combination of claim 1 wherein the base portion of the carrier foot comprises at least two planar members for application on a flat surface.

3. The combination of claim 2, wherein the support means of the body portion of the separate carrier foot includes a recess for receiving a portion of the closing stopper.

4. The combination of claim 2, wherein the closing stopper includes a recess for receiving a portion of the carrier foot support means.

5. In a blood vessel access device that includes a tubular body for delivering a fluid and a separate closing stopper, the tubular body having a housing, a distal end and a proximal end, the distal end including a distal port for receiving the closing stopper and the proximal end including a needle the improvement which comprises a fitting associated with the housing and comprising support means for temporarily holding the closing stopper when the closing stopper is removed from the distal port of the blood vessel access device.

6. The device of claim 5 wherein the which fitting is an embossment which is integral with the housing of the tubular body.

7. The device of claim 5 which further comprises a carrier-stopper adapted to close the distal port, said carrier-stopper having an upper surface with a recess, wherein the support means of the fitting comprises an extension which is adapted to be received by the recess of the carrier-stopper.

8. The device of claim 5 wherein the support means of the fitting comprises a specially-designed carrier-stopper adapted for closing the distal port, wherein the specially-designed carrier-stopper has an upper part configured to support the closing stopper.

9. The device of claim 8 wherein the upper part of the specially-designed carrier stopper has a recess for receiving a portion of the closing stopper.

10. The device of claim 8, wherein the closing stopper has a recess for receiving the upper part of the specially-designed carrier stopper.

11. The device of claim 5 which further comprises a carrier-stopper adapted to close the distal port, wherein the support means of the fitting comprises a mid-piece having an upper part configured to engage the closing stopper; and a lower part configured for attachment to the carrier stopper.

12. The device of claim 11, wherein the upper part of the mid-piece includes a recess for receiving a portion of the closing stopper.

13. The device of claim 11, wherein the closing stopper includes a recess for receiving a portion of the upper part of the mid-piece.

14. The device of claim 11, wherein the lower part of the mid-piece has a recess that receives a portion of the carrier stopper.

15. The device of claim 11, wherein the carrier stopper has a recess that receives a portion of the lower part of the mid-piece.

16. The device of claim 5 wherein the fitting comprises a rider associated with the tubular body and having an lower part and a upper part, wherein the lower part is provided with a recess for engaging the housing of the tube body, and wherein the upper part is configured to support the closing stopper.

17. The device of claim 16 wherein the upper part of the rider has a recess for receiving a portion of the closing stopper.

18. The device of claim 16 wherein the closing stopper has a recess for receiving a portion of the upper part of the rider.

19. The device of claim 5 which further comprises a carrier-stopper adapted to close the distal port, wherein the carrier-stopper includes a guide rail to facilitate the insertion of the closing stopper therein.

* * * * *